US010975044B2

(12) United States Patent
Fedurco et al.

(10) Patent No.: US 10,975,044 B2
(45) Date of Patent: Apr. 13, 2021

(54) HALOGENATED BENZOXAZINE FOR USE IN THE SYNTHESIS OF POLYBENZOXAZINE

(71) Applicant: COMPAGNIE GENERALE DES ETABLISSEMENTS MICHELIN, Clermont-Ferrand (FR)

(72) Inventors: Milan Fedurco, Clermont-Ferrand (FR); Marco Ribezzo, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 16/616,266

(22) PCT Filed: May 24, 2017

(86) PCT No.: PCT/FR2017/051293
§ 371 (c)(1),
(2) Date: Nov. 22, 2019

(87) PCT Pub. No.: WO2018/215701
PCT Pub. Date: Nov. 29, 2018

(65) Prior Publication Data
US 2020/0087268 A1 Mar. 19, 2020

(51) Int. Cl.
C07D 263/62 (2006.01)

(52) U.S. Cl.
CPC .................. C07D 263/62 (2013.01)

(58) Field of Classification Search
CPC .................................... C07D 263/62
See application file for complete search history.

(56) References Cited

U.S. PATENT DOCUMENTS

| 3,126,290 | A | 3/1964 | Hemwall |
| 5,543,516 | A | 8/1996 | Ishida |
| 9,255,075 | B2 * | 2/2016 | Ward .................. C08G 73/026 |
| 9,617,372 | B2 | 4/2017 | Fedurco et al. |
| 9,845,376 | B2 | 12/2017 | Fedurco et al. |
| 10,150,833 | B2 | 12/2018 | Fedurco et al. |
| 2015/0259463 | A1 | 9/2015 | Fedurco et al. |
| 2015/0274878 | A1 | 10/2015 | Fedurco et al. |
| 2016/0122460 | A1 | 5/2016 | Fedurco et al. |
| 2018/0370284 | A1 | 12/2018 | Fedurco et al. |
| 2019/0300765 | A1 | 10/2019 | Fedurco et al. |
| 2020/0095211 | A1 | 3/2020 | Fedurco et al. |
| 2020/0095458 | A1 | 3/2020 | Fedurco et al. |
| 2020/0115394 | A1 | 4/2020 | Fedurco et al. |
| 2020/0199112 | A1 | 6/2020 | Fedurco et al. |
| 2020/0208010 | A1 | 7/2020 | Fedurco et al. |
| 2020/0290402 | A1 | 9/2020 | Fedurco et al. |

FOREIGN PATENT DOCUMENTS

| CN | 103058948 A | 4/2013 |
| WO | 2010/002872 A2 | 1/2010 |
| WO | 2013/148408 A1 | 10/2013 |
| WO | 2014/063963 A1 | 5/2014 |
| WO | 2014/063968 A1 | 5/2014 |
| WO | 2014/173838 A1 | 10/2014 |
| WO | 2014/173839 A1 | 10/2014 |
| WO | 2017/103376 A1 | 6/2017 |
| WO | 2018/078227 A1 | 5/2018 |
| WO | 2018/078228 A1 | 5/2018 |

OTHER PUBLICATIONS

International Search Report dated Sep. 5, 2017, in corresponding PCT/FR2017/051293 (4 pages).
Y. Yagci, et al., "Recent Advancement on Polybenzoxazine—A Newly Developed High Performance Thermoset", J. Polymer Sci.: Part A: Polymer Chem., vol. 47, No. 21, pp. 5565-5576 (2009).
C.R. Arza, et al., "Quantifying Dispersion in Graphene Oxide/Reactive Benzoxazine Monomer Nanocomposites", Macromolecules, vol. 47, pp. 3685-3692 (2014).
B. Kiskan, et al., "Synthesis, Characterization, and Properties of New Thermally Curable Polyetheresters Containing Benzoxazine Moieties in the Main Chain", J. Polymer Sci.: Part A: Polymer Chem., vol. 46, pp. 414-420 (2008).
N.N. Ghosh, et al, "Polybenzoxazines—New high performance thermosetting resins: Synthesis and properties", Prog. Polym. Sci., vol. 32, pp. 1344-1391 (2007).
Copending U.S. Appl. No. 16/621,570, filed Dec. 11, 2019 (available on USPTO system).

* cited by examiner

Primary Examiner — Yong L Chu
(74) Attorney, Agent, or Firm — Venable LLP

(57) ABSTRACT

A halogenated benzoxazine compound, which can be used in particular as monomer in the synthesis of polybenzoxazine, corresponds to the formula:

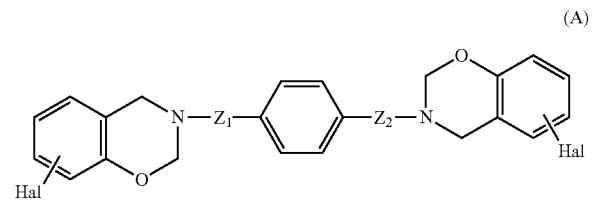

(A)

in which: each benzene nucleus of the two oxazine rings bears at least one halogen (represented by the symbol Hal), in particular bromine, chlorine or fluorine; and $Z_1$ and $Z_2$, which are identical or different, represent an aliphatic, at least divalent, bonding group comprising at least one carbon atom and optionally at least one heteroatom chosen from O, S, N and P.

20 Claims, 11 Drawing Sheets

HALOGENATED BENZOXAZINE FOR USE IN THE SYNTHESIS OF POLYBENZOXAZINE

1. FIELD OF THE INVENTION

The present invention relates to monomers which can be used in the synthesis of thermosetting resins, intended in particular for adhesive systems which make possible in particular the adhesive bonding of metal to rubber.

It more particularly relates to benzoxazine compounds suitable for the synthesis of polybenzoxazines which can be used in particular as adhesive layers in metal/rubber composites intended for the manufacture of rubber articles, such as pneumatic or non-pneumatic tyres, for vehicles.

2. STATE OF THE ART

Metal/rubber composites, in particular for vehicle tyres, are well known. They are most often composed of a matrix made of rubber, generally diene rubber, which can be crosslinked with sulfur, comprising metal reinforcing elements (or "reinforcers"), such as threads, films or cords made of carbon steel.

As they are subjected to very high stresses during the rolling of the tyres, in particular to repeated actions of compression, bending or variation in curvature, these composites must, in a known way, satisfy a large number of sometimes contradictory technical criteria, such as uniformity, flexibility, flexural strength and compressive strength, tensile strength, wear resistance and corrosion resistance, and must maintain these performance qualities at a very high level for as long as possible.

It is easily understood that the adhesive interphase between rubber and reinforcers plays a dominating role in the endurance of these performance qualities. The conventional process for connecting the rubber compositions to carbon steel consists in coating the surface of the steel with brass (copper/zinc alloy), the bonding between the steel and the rubber matrix being provided by sulfurization of the brass during the vulcanization or curing of the rubber. In order to improve the adhesion, use is generally made, in addition, in these rubber compositions, of organic salts or metal complexes, such as cobalt salts, as adhesion-promoting additives.

In point of fact, it is known that the adhesion between the carbon steel and the rubber matrix is liable to weaken over time as a result of the gradual development of the sulfides formed, under the effect of the various stresses encountered, in particular mechanical and/or thermal stresses, it being possible for the above degradation process to be accelerated in the presence of moisture. Moreover, the use of cobalt salts renders the rubber compositions more sensitive to oxidation and to ageing, and significantly increases the cost thereof, not to mention that it is desirable to eliminate, in the long run, the use of such cobalt salts in rubber compositions due to recent developments in European regulations relating to metal salts of this type.

For all the reasons set out above, manufacturers of metal/rubber composites, in particular vehicle tyre manufacturers, are seeking novel adhesive solutions in order to adhesively bond the metal reinforcers to the rubber compositions, while overcoming, at least in part, the abovementioned disadvantages.

Thus it is that the recently published applications WO 2014/063963, WO 2014/063968, WO 2014/173838 and WO 2014/173839, filed by the Applicant Companies, have described novel polymers comprising urea, urethane or thiourea units, and also their starting monomers, which meet the above objectives. Used in particular as adhesion primer on metal in metal/rubber composites, these polymers make it possible very advantageously to adhesively bond the metal to the rubber matrices by subsequently using simple textile adhesives, such as "RFL" (resorcinol/formaldehyde latex) adhesives or other equivalent adhesive compositions, or else directly (that is to say, without employing such adhesives) to these rubber matrices when the latter contain, for example, appropriate functionalized unsaturated elastomers, such as epoxidized elastomers. Thus, the cobalt salts (or other metal salts) can in particular be dispensed with in the rubber compositions intended to be connected to brass-coated metal reinforcers.

On continuing their research studies, the Applicant Companies have found a novel benzoxazine compound, which can be used as monomer in the synthesis of a polybenzoxazine, of the thermosetting type, which, at ambient temperature, exhibits the same adhesive performance qualities, with regard to the metal and the rubber, as the abovementioned polymers but which exhibits, once thermoset (crosslinked), a thermal and chemical stability which is again improved and the specific microstructure of which additionally makes it possible very advantageously to adjust the flexibility of the molecule according to the particular applications targeted.

3. SUMMARY OF THE INVENTION

The present invention relates to a halogenated benzoxazine corresponding to the formula (the symbol "Hal" representing a halogen):

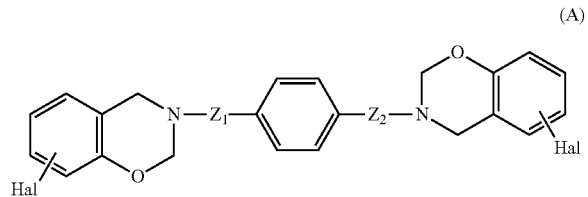

(A)

in which:
  each benzene nucleus of the two oxazine rings bears at least one halogen;
  $Z_1$ and $Z_2$, which are identical or different, represent an aliphatic, at least divalent, bonding group comprising at least one carbon atom and optionally at least one heteroatom chosen from O, S, N and P.

By virtue of this specific benzoxazine, it is possible to prepare benzoxazine polymers or "polybenzoxazines" which have the remarkable ability, at high temperature, to open their oxazine rings and to thus result in a thermosetting polyphenol resin structure. This confers on them, in comparison with the other known polymers described in the introduction to the present document, a better thermal stability. Finally, its specific microstructure makes it possible very advantageously to adjust the flexibility of the polybenzoxazines depending on the particular applications targeted.

The invention also relates to the use of a compound in accordance with the invention in the synthesis of a polybenzoxazine, and also to any polybenzoxazine resulting from at least one benzoxazine compound according to the invention.

The invention also relates to any process for the synthesis of a polybenzoxazine by polycondensation of a compound according to the invention, in particular with, as second monomer, an aromatic diol or thiol compound.

4. BRIEF DESCRIPTION OF THE FIGURES

The invention and its advantages will be easily understood in the light of the detailed description and of the implementational examples which follow, and also of FIGS. 1 to 11 relating to these examples, which represent or diagrammatically represent:

- the general principle for the synthesis of a benzoxazine compound starting from three compounds, phenol, formaldehyde and amine (R=residue of the amine) (FIG. 1a);
- the mechanism for opening, by heat input, the oxazine ring (ring-opening) of such a benzoxazine compound (FIG. 1b);
- a general scheme for the synthesis, starting from a halogenated phenol (Hal representing a halogen), paraformaldehyde and a specific aromatic diamine, of a halogenated benzoxazine in accordance with the invention of formula (A), which can be used as monomer (Monomer denoted "M") in the synthesis of a polybenzoxazine (FIG. 2);
- a possible scheme for the synthesis, starting from a halogenated phenol, paraformaldehyde and a specific diamine of the aromatic type, of a particular halogenated benzoxazine according to the invention of formula (A-1), which can be used as monomer (Monomer denoted M-1) in the synthesis of a particular polybenzoxazine (FIG. 3);
- a general scheme for the synthesis of a polybenzoxazine polymer (Polymer denoted "P") starting from the halogenated benzoxazine of the invention of formula (A) (Monomer M) of FIG. 2 and another monomer of generic formula (B) (Monomer denoted "N") of aromatic diol or thiol type (FIG. 4);
- a scheme for the synthesis of a particular polybenzoxazine polymer (Polymer denoted P-1), starting from a particular halogenated benzoxazine according to the invention of formula (A-2) (Monomer M-2) and another particular monomer of formula (B-1) (Monomer N-1) of the sulfur-comprising aromatic diol type (bearing a thioether functional group) (FIG. 5);
- a scheme for the synthesis of another polybenzoxazine (Polymer denoted P-2), starting from the particular halogenated benzoxazine according to the invention of formula (A-2) (Monomer M-2) of the preceding FIG. 5 and another particular monomer of formula (B-2) (Monomer N-2) of the aromatic thiol type (bearing an ether functional group) (FIG. 6);
- a scheme for the synthesis of another polybenzoxazine (Polymer denoted P-3), starting from the halogenated benzoxazine according to the invention of formula (A-2) (Monomer M-2) and another particular monomer of formula (B-3) (Monomer N-3) of the aromatic thiol type (bearing a thioether functional group) (FIG. 7);
- the polybenzoxazine (Polymer denoted P' here) of FIG. 4 once its oxazine rings have been opened after heat treatment of the Polymer P (FIG. 8);
- the particular polybenzoxazine (Polymer denoted P-1') of FIG. 5, once its oxazine rings have been opened after heat treatment of the Polymer P-1 (FIG. 9);
- the scheme for the synthesis, starting from a brominated phenol (compound 1), paraformaldehyde (compound 2) and a specific aromatic diamine (compound 3), of a particular brominated dibenzoxazine according to the invention of formula (A-3) (Monomer denoted M-3) which can be used in the synthesis of polybenzoxazines (Polymer P-4 and P-4' of FIG. 11) (FIG. 10);
- the scheme for the synthesis of a particular polybenzoxazine (Polymer denoted P-4), starting from the particular halogenated benzoxazine according to the invention of formula (A-3) (Monomer M-3) of the preceding FIG. 10 and the particular monomer of formula (B-1) (Monomer N-1), and also the structure of this polymer once its oxazine rings have been opened (Polymer denoted P-4') (FIG. 11).

5. DETAILED DESCRIPTION OF THE INVENTION

It will first of all be recalled that benzoxazines are compounds of general formula:

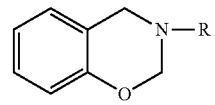

The appended FIG. 1a recalls the general principle of the synthesis of a benzoxazine, in this instance starting (condensation reaction) from one molecule of phenol, from two molecules of formaldehyde and from an amine (R denoting the residue of the amine), with elimination of two molecules of water.

FIG. 1b for its part recalls the mechanism for opening the oxazine ring (ring-opening) of such a compound during a heat input (represented by the symbol Δ).

Numerous benzoxazine compounds or monomers can thus be synthesized using various phenols and amines depending on their types of substituents. These substituting groups may subsequently provide polymerizable sites and make possible the synthesis of various benzoxazine polymers (or polybenzoxazines).

Benzoxazines and polybenzoxazines which result therefrom are products which are today well known to a person skilled in the art; to cite but a few publication examples, mention may be made of the papers "*Polybenzoxazines—New high performance thermosetting resins: synthesis and properties*"; N. N. Ghosh et al., Prog. Polym. Sci., 32 (2007), 1344-1391, or "*Recent Advancement on Polybenzoxazine—A Newly Developed High Performance Thermoset*", Y. Yaggi et al., J. Polym. Sci. Part A: Polym. Chem., Vol. 47 (2009), 5565-5576, and also, for example, of the patents or patent applications U.S. Pat. No. 5,543,516 and WO 2013/148408.

As explained in detail in the above documents, polybenzoxazines have the remarkable ability, at high temperature (for example, typically greater than 150° C., indeed even greater than 200° C., depending on their particular microstructure), to open their oxazine rings and to thus result in thermosetting polyphenol resin structures.

The specific benzoxazine of the invention, designated "Monomer M" in the present patent application, is of the halogenated type; it corresponds to the generic formula (A) which follows, Hal representing a (at least one, that is to say one or more) halogen:

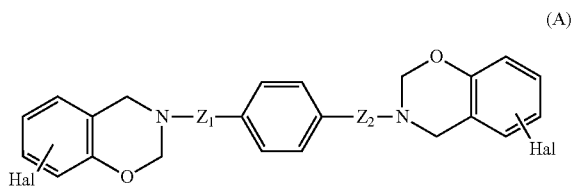

(A)

The appended FIG. 2 gives the general scheme for the synthesis thereof, under heat input and with elimination of water, starting from a halogenated phenol, paraformaldehyde and a diamine.

In the formula (A) above, $Z_1$ and $Z_2$, which are identical or different, represent a bonding (spacer) group which is at least divalent, that is to say that they might comprise more than two covalent bonds, for example three or four covalent bonds. Preferably, $Z_1$ and $Z_2$ are divalent, that is to say comprise only two covalent bonds.

$Z_1$ and $Z_2$ are aliphatic. These groups, which can be ethylenically saturated or unsaturated, comprise, by definition, at least one (that is to say, one or more) carbon atom, and optionally at least one (that is to say, one or more) heteroatom chosen from O (oxygen), S (sulfur), N (nitrogen) and P (phosphorus).

According to a particular embodiment of the invention, $Z_1$ and $Z_2$, which are identical or different, represent an aliphatic group comprising from 1 to 12, more preferably from 1 to 8, in particular from 1 to 6, carbon atoms. More preferably still, $Z_1$ and $Z_2$, which are identical or different, represent a (poly)alkylene (or alkylidene) sequence comprising from 1 to 8, preferably from 1 to 6, in particular from 1 to 4, carbon atoms.

More particularly, the compound of the invention corresponds to the formula:

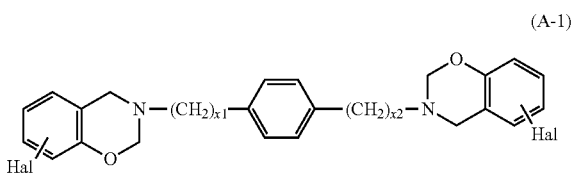

(A-1)

in which $x_1$ and $x_2$, which are identical or different, represent an integer from 1 to 8, preferably from 1 to 6, in particular from 1 to 4.

Each benzene nucleus of the two oxazine rings of the Monomer M bears at least one (that is to say, one or more) halogen, this halogen preferably being bromine (Br), chlorine (Cl) or fluorine (F), more preferably bromine.

Moreover, in this monomer of formula (A), one or more hydrogen atoms of at least one or of each of these benzene nuclei can be substituted (or not) by various substituents, for example by functional groups capable of promoting the adhesion of the polymer to the metal and/or to the rubber. Likewise, at least one (that is to say, one or more) hydrogen atom of the phenylene group (or central benzene nucleus positioned between $Z_1$ and $Z_2$) might also be substituted by different substituents, for example by such functional groups also capable of promoting the adhesion of the polymer to the metal and/or to the rubber.

Preferably, each benzene nucleus of the two oxazine rings of the compound according to the invention bears a single halogen (Hal) or at most two, more preferably one and only one halogen, the latter being more preferably located in the para position with respect to the oxygen of the oxazine ring.

Thus, according to a particularly preferred embodiment, the compound of the invention corresponds to the formula:

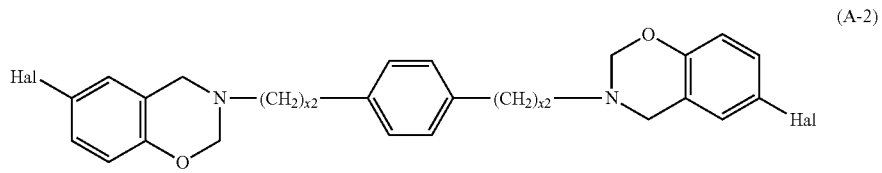

(A-2)

in which $x_1$ and $x_2$, which are identical or different, represent an integer from 1 to 8, preferably from 1 to 6.

According to a particularly preferred embodiment, Hal represents bromine.

FIG. 3 illustrates a possible scheme for the synthesis, starting from a specific diamine of the aromatic type, of a particular halogenated benzoxazine according to the invention of formula (A-1), this benzoxazine being able to be used as monomer (Monomer denoted M-1) in the subsequent synthesis of a polybenzoxazine. It is noted that, $Z_1$ and $Z_2$ represent —(CH2)x1- and —(CH2)x2- respectively vary, in which formulae the symbols "x1" and "x2" represent an integer preferably ranging from 1 to 12, more preferably from 1 to 8, in particular from 1 to 6. Such a synthesis will be described in greater detail in the implementational examples which follow (FIG. 10).

The benzoxazine in accordance with the invention of formula (A) described above is intended in particular (as Monomer M) for the synthesis of a polybenzoxazine by polycondensation, in particular by polycondensation with at least one aromatic diol or thiol compound as second monomer ("Monomer N") having the formula (B):

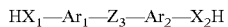

in which:
  $X_1$ and $X_2$, which are identical or different, represent O (oxygen; case of a diol monomer) or S (sulfur; case of a thiol monomer);
  $Ar_1$ and $Ar_2$, which are identical or different, represent a phenylene group;
  $Z_3$ represents O or $(S)_n$, the symbol "n" representing an integer equal to 1 (case of a single sulfur atom) or greater than 1 (case of several sulfur atoms).

In the generic formula (B) above, there is preferably at least one of the following characteristics which is confirmed:
  $X_1$ and $X_2$ each represent either a sulfur atom or an oxygen atom;
  $Z_3$ represents O or S (i.e. "n" equal to 1), more preferably S.

More preferably, it is all of the preferred characteristics above which are confirmed simultaneously.

Moreover, in the formula (B) above, one or more hydrogen atoms of at least one or of each $Ar_1$ and $Ar_2$ group can be substituted (or not) by a single or several substituents, which are identical or different, for example by functional groups capable of promoting the adhesion of the polymer to the metal and/or to the rubber.

Mention may be made, as examples of Monomers N (diols or thiols) preferably suitable for the invention, of the Monomers respectively denoted N-1, N-2 and N-3 in FIGS. 5, 6 and 7, which figures are commented on subsequently, which monomers are of respective formulae (B-1), (B-2) and (B-3) below:

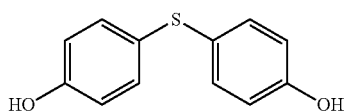
(B-1)

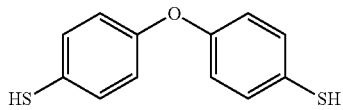
(B-2)

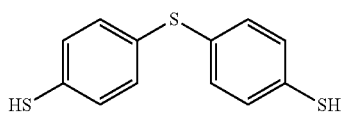
(B-3)

Thus, the benzoxazine in accordance with the invention of formula (A) is intended in particular for the synthesis of a polybenzoxazine (Polymer denoted "P") comprising repeating structural entities comprising at least one unit corresponding to the formula (I) (before opening of the oxazine rings) or formula (II) (after opening of the rings) below:

Polymer should be understood here as meaning any homopolymer or copolymer, in particular block copolymer, with repeating structural entities comprising at least one unit of formula (I) or (II) above; this polymer can, of course, comprise both units of formula (I) and units of formula (II).

In the formula (II) above, a person skilled in the art will immediately understand that the two symbols "*" (which are identical or different) represent any attachment of the unit to a carbon atom or to a heteroatom (preferably chosen from O, S, N and P), which attachment or bond results from the opening of the oxazine rings.

FIG. 4 represents a general scheme for the synthesis, by polycondensation, of such a polybenzoxazine (Polymer P), starting from the halogenated benzoxazine according to the invention of formula (A) of FIG. 2 (Monomer M) and from another monomer, of generic formula (B), which is of the aromatic diol or thiol type (Monomer N).

The polybenzoxazine of FIG. 4, more precisely at least a portion of its repeating entities, has also been represented in FIG. 8, before (Polymer P) and after (Polymer P') opening of the oxazine rings.

FIG. 5 represents a particular scheme for the synthesis of a specific polybenzoxazine (Polymer denoted P-1) of formula (I-1), starting from a particular halogenated benzoxazine according to the invention (Monomer M-2) of formula (A-2) and from another specific monomer (Monomer N-1) of formula (B-1) of the sulfur-comprising aromatic diol type (4,4'-thiodiphenol).

In this example, it is noted in particular, according to a preferred embodiment of the invention already described, that each benzene nucleus of the benzoxazine (Monomer M-2) in accordance with the invention bears one and only one halogen (Hal), more preferably bromine, this halogen being more particularly located in the para position with respect to the oxygen of the oxazine ring.

This polybenzoxazine of FIG. 5, or more precisely at least a portion of its repeating entities, has also been represented in FIG. 9, before (Polymer P-1) and after (P-1') opening of its oxazine rings following a sufficient heat input.

Thus, according to a particularly preferred embodiment, the polybenzoxazine resulting from the benzoxazine of the invention is characterized by repeating entities comprising at

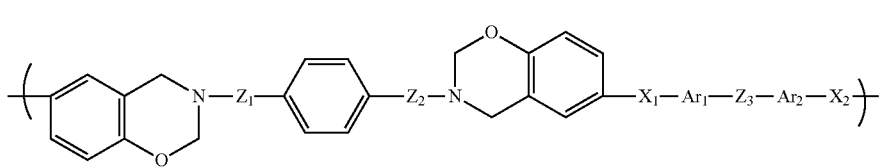
(I)

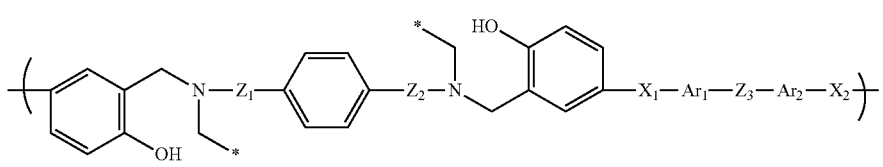
(II)

in which formulae (I) and (II) above $Z_1$, $Z_2$ and $Z_3$ have the main definition and the preferred definitions already given above.

least one unit corresponding to the particular formulae (I-1) (before opening of the benzoxazine rings) or (II-1) (after opening of the rings):

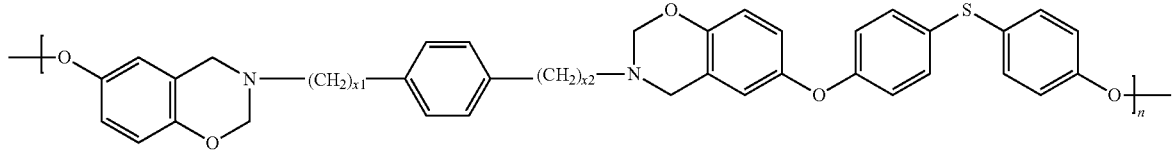

(I-1)

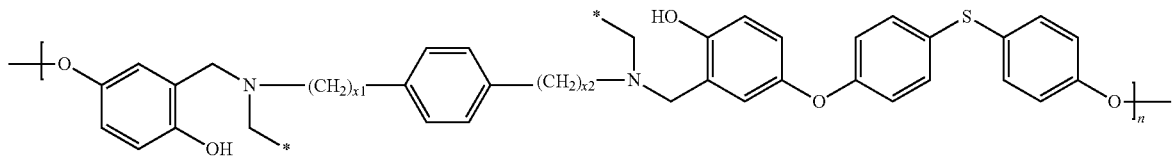

(II-1)

Figure 5:
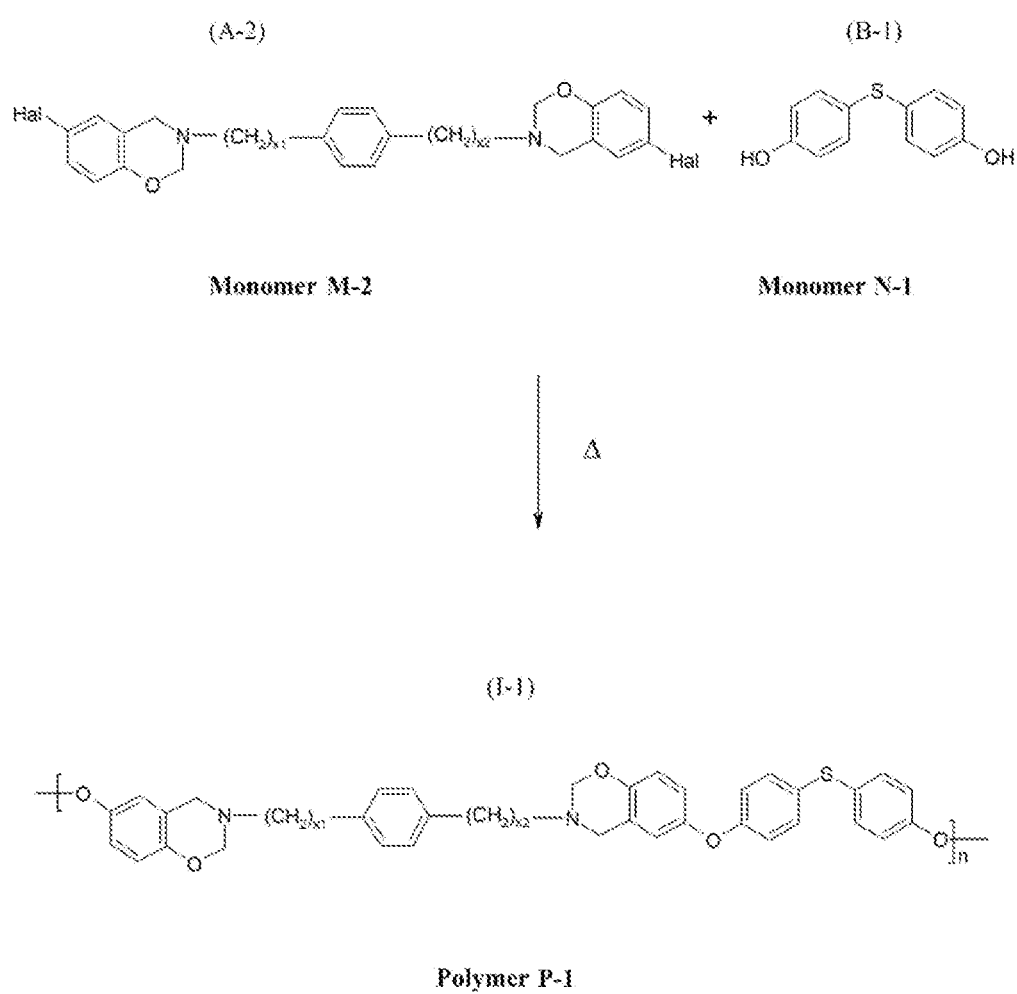
Figure 6:
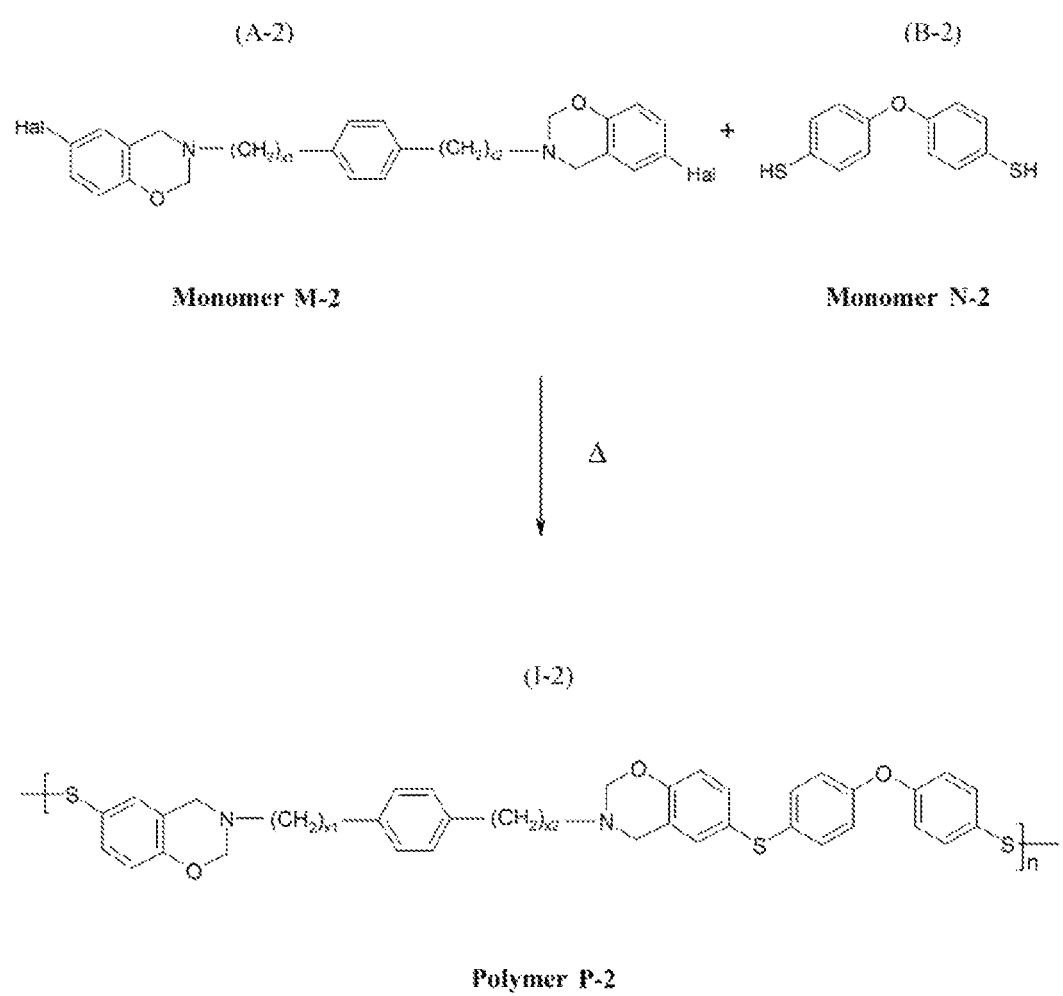
FIG. 6 represents another scheme for the particular synthesis of another specific polybenzoxazine (Polymer denoted P-2) of formula (I-2), starting from the preceding specific halogenated benzoxazine of the invention (Monomer M-2) and from another specific monomer (Monomer N-2) of formula (B-2) of the aromatic thiol type (additionally bearing an ether functional group).
Figure 7:
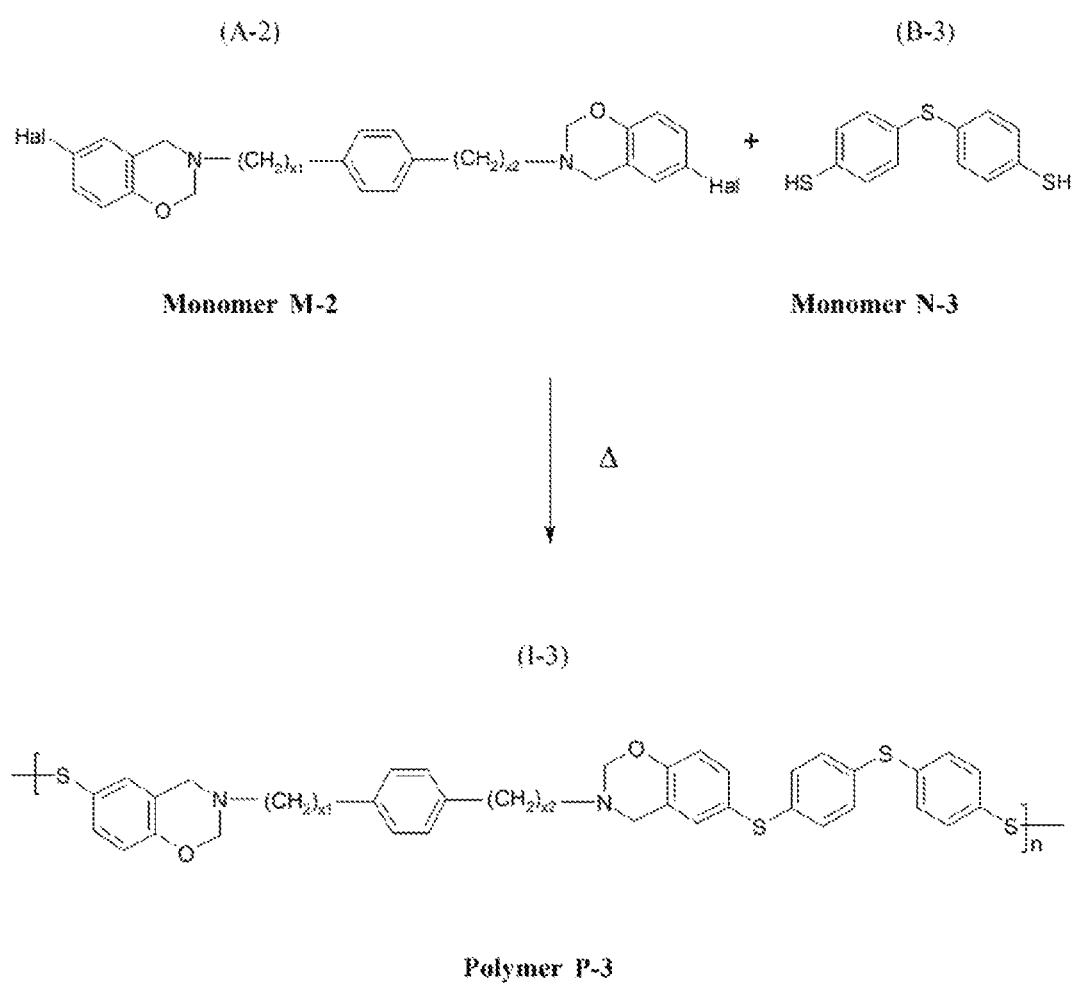
FIG. 7 represents another scheme for the particular synthesis of another specific polybenzoxazine (Polymer denoted P-3) of formula (I-3), starting from the preceding specific halogenated benzoxazine of the invention (Monomer M-2) and from another specific monomer (Monomer N-3) of the aromatic thiol type (additionally bearing a thioether functional group).

In these examples of FIGS. 6 and 7, as for the preceding FIG. 5, it is noted in particular, according to a preferred embodiment of the invention already indicated, that each benzene nucleus of the two oxazine rings of the benzoxazine of the invention bears one and only one halogen (Hal), more preferably bromine, more particularly located in the para position with respect to the oxygen of the oxazine ring.

Figure 1A:
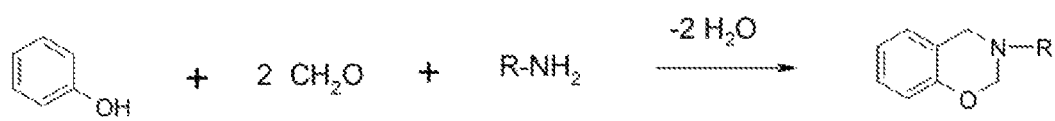
Figure 1B:
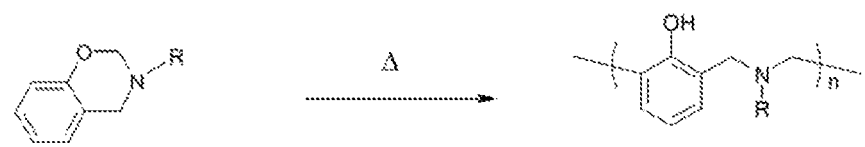
Figure 2:
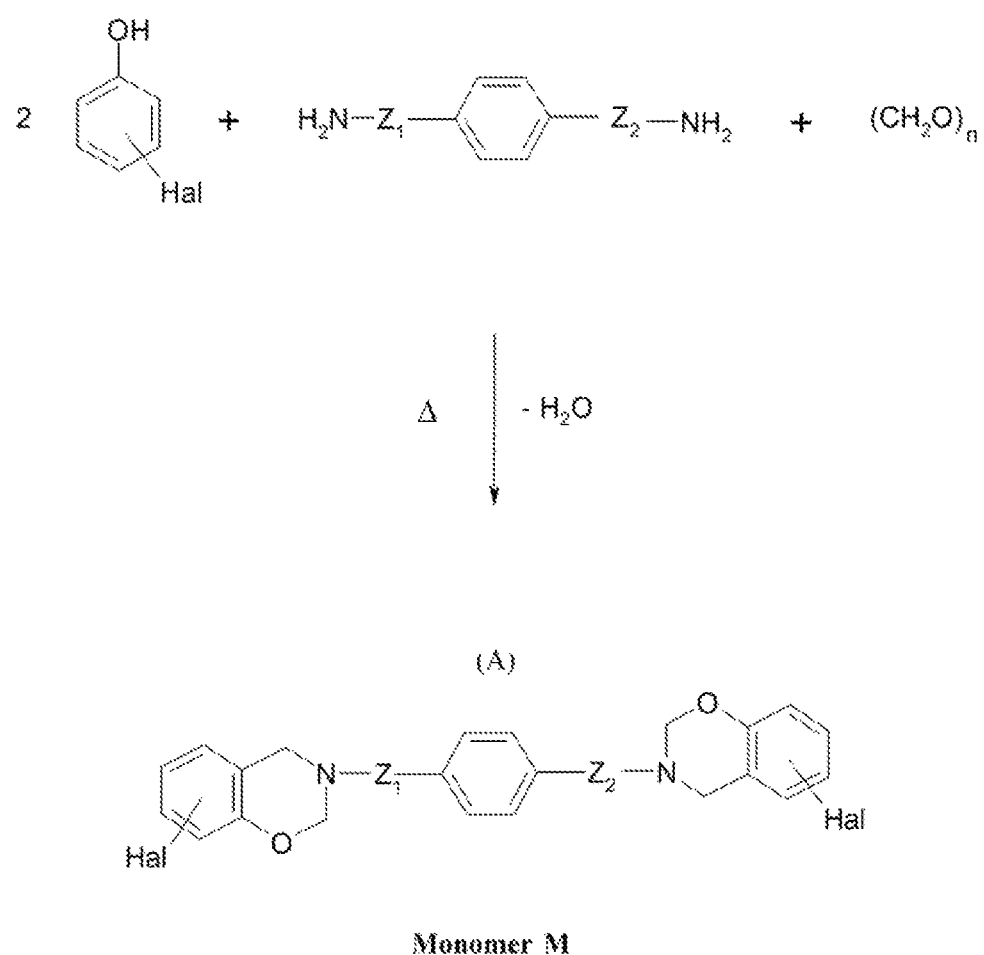
Figure 3:
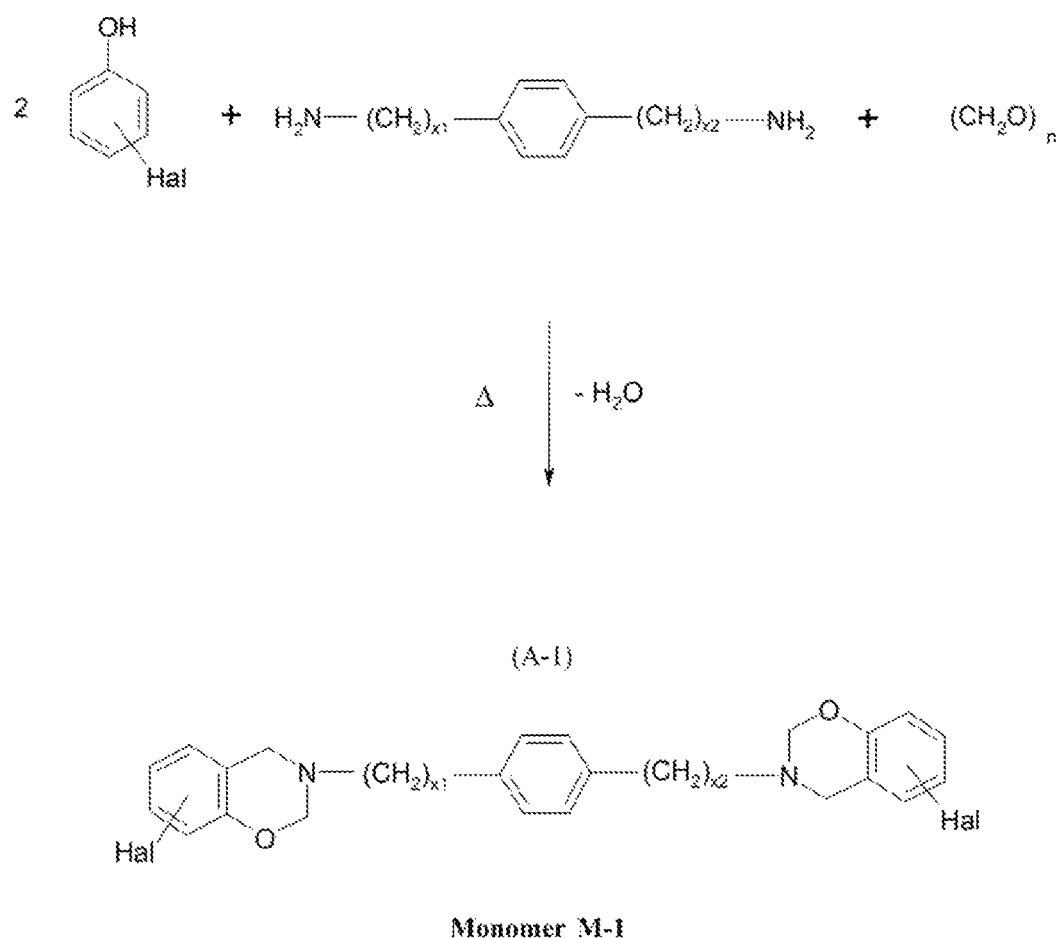
Figure 4:
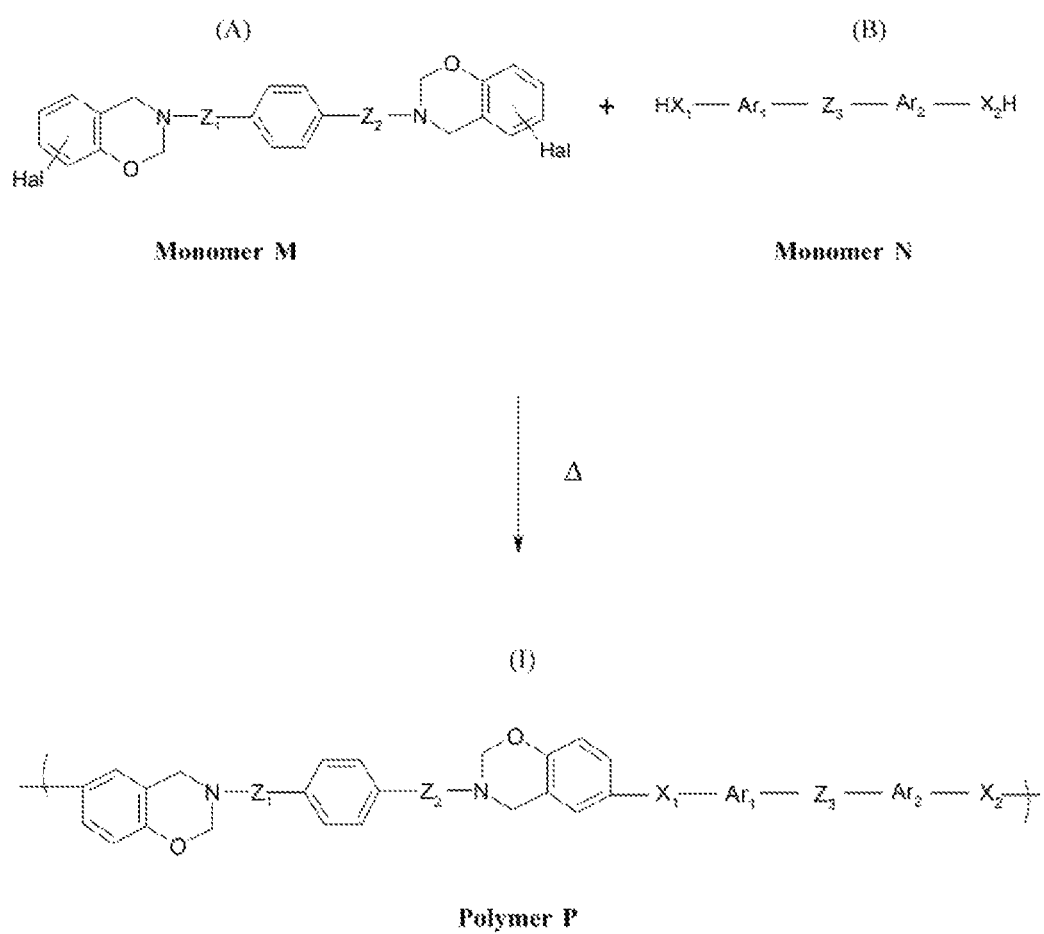
Figure 8:
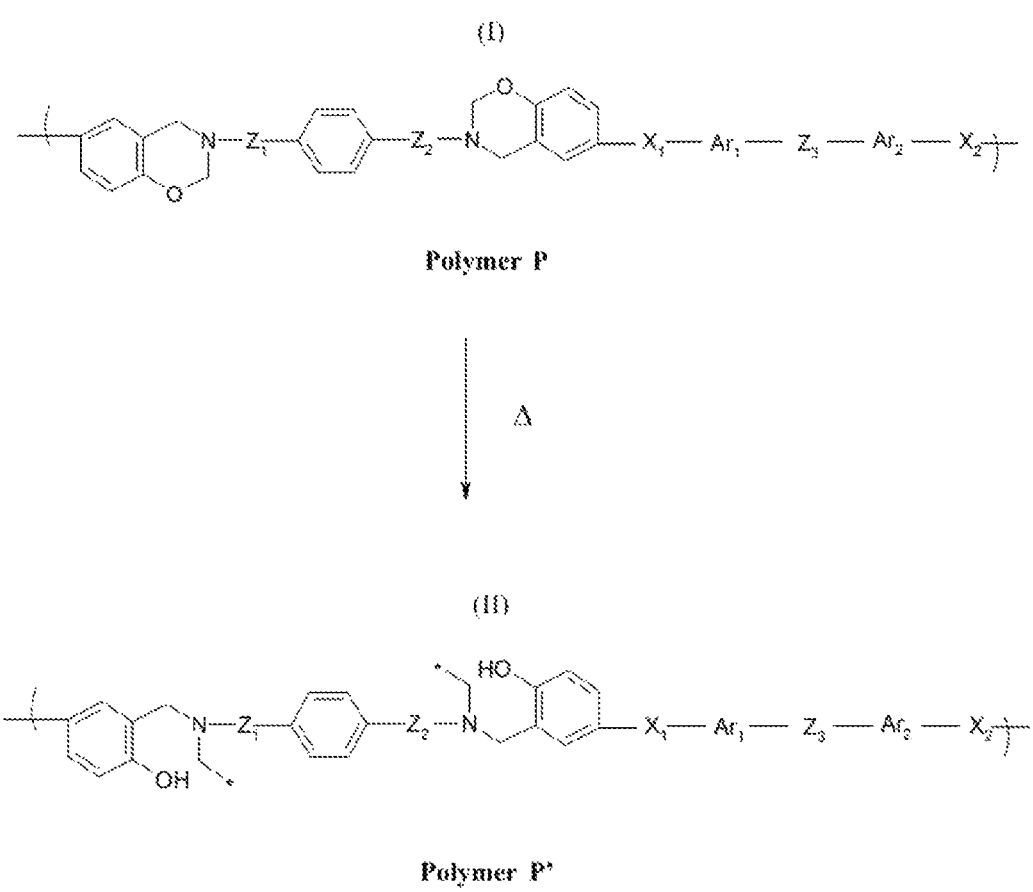
Figure 9:
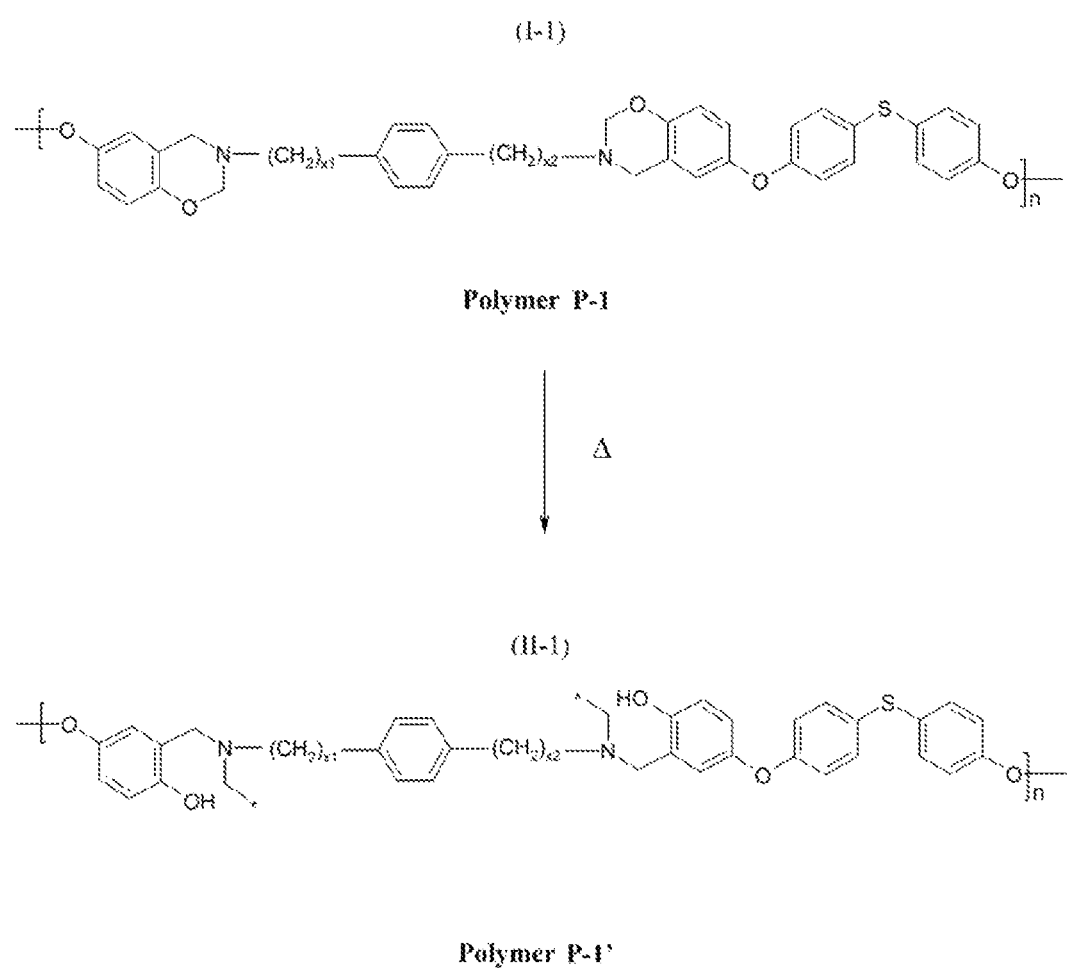

As already indicated, FIGS. 8 and 9 also represent the polybenzoxazines respectively denoted P' and P-1' of FIG. 4 and FIG. 5, once their oxazine rings are open.

Typically, the polybenzoxazine resulting from the benzoxazine compound of the invention can comprise from ten to several hundred, preferably from 50 to 300, structural entities having units of formula (I) and/or (II), in particular structural entities as represented by way of examples in FIGS. 5 to 9 and 11.

This polybenzoxazine resulting from the benzoxazine of the invention can advantageously be used, as adhesion primer or as sole adhesive layer, in order to coat a metal substrate, at the very least a substrate of which at least the surface is at least partially metallic, and to cause the substrate to adhere to rubber. It can very particularly be used on any type of metal reinforcer, such as, for example, a thread, a film or a cord made of steel, in particular of carbon steel, intended in particular to reinforce a matrix of unsaturated rubber, such as natural rubber. Any known adhesive system, for example a conventional textile adhesive of the RFL (resorcinol/formaldehyde latex) type, can also be used to cause the rubber to adhere to the polybenzoxazine layer. A person skilled in the art will readily understand that the connection between the metal substrate provided with its polybenzoxazine layer and the rubber layer with which it is in contact will be definitively provided during the final curing (crosslinking) of the rubber article in question.

6. EXAMPLES OF THE INVENTION

In the present patent application, unless expressly indicated otherwise, all the percentages (%) shown are % by weight.

The tests which follow describe first of all the synthesis of a preferred benzoxazine compound (Monomer M-3) in accordance with the invention, of formula:

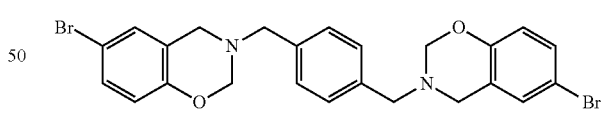

(A-3)

Then, the synthesis is described, starting from this monomer M-3, of a polybenzoxazine (Polymer P-4) of formula (I-4):

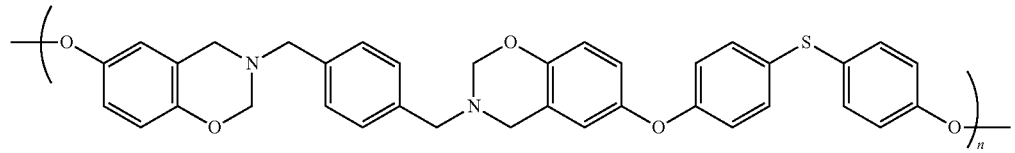

(I-4)

Finally, adhesion tests are carried out in order to illustrate the excellent adhesive performance of the polybenzoxazines resulting from the benzoxazines of the invention.

5.1. Synthesis of a Halogenated Benzoxazine in Accordance with the Invention (Monomer M-3)

For this synthesis, a 250-ml three-necked round-bottomed flask, equipped with a thermometer, a nitrogen inlet, a magnetic stirrer and a condenser, is provided.

Figure 10:
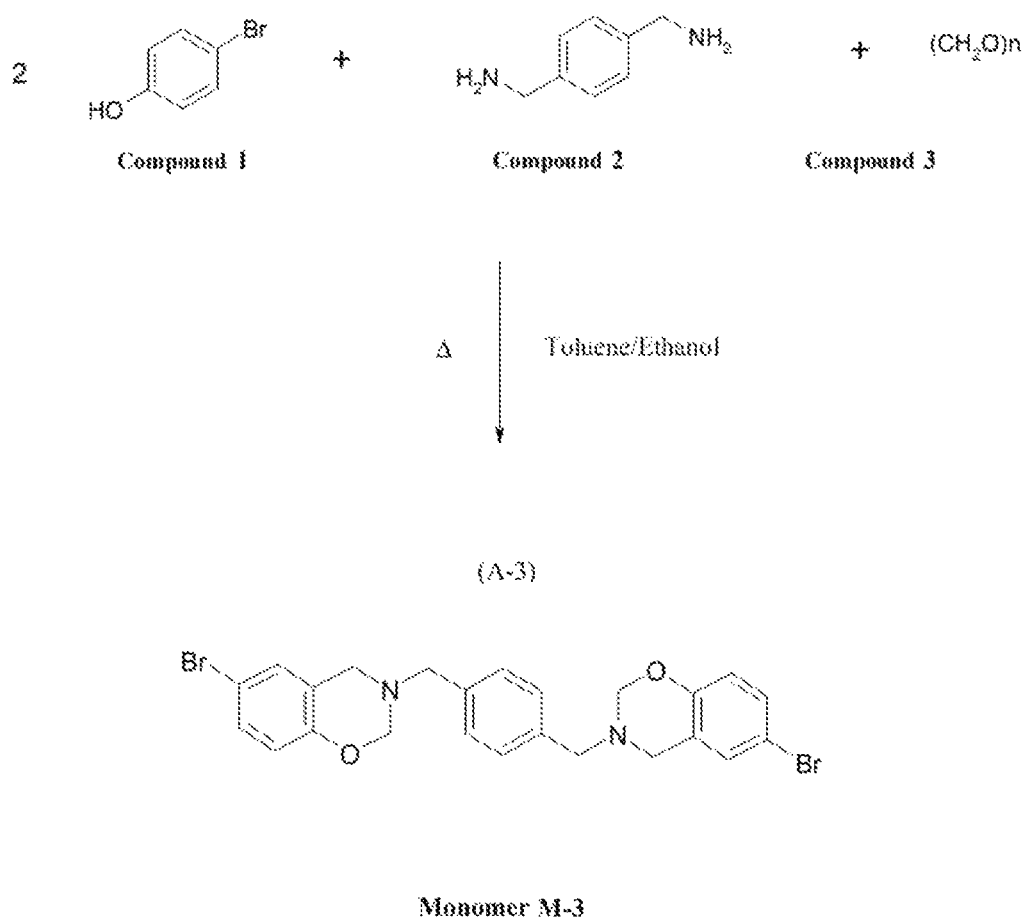

The synthesis is carried out according to the procedure diagrammatically represented in FIG. 10, as explained in detail below, starting from three compounds: a halogenated phenol (compound 1; 4-bromophenol; Aldrich product B75808), an aromatic diamine (compound 2; p-xylylenediamine; TCI Europe product D1018) and paraformaldehyde (compound 3; Aldrich product 158127), in the presence of two solvents (anhydrous toluene and anhydrous ethanol).

Compound 1 (2 eq., 10.38 g, i.e. 60 mmol) and then ethanol (51 ml) are poured into the round-bottomed flask. The presence of ethanol is important here, preventing the formation of an unstable intermediate of the triazine type. Compound 2 (1 eq., 4.13 g, i.e. 30 mmol), compound 3 (4 eq., 3.60 g, i.e. 120 mmol) and finally the toluene (102 ml) are subsequently introduced with stirring. The reaction medium is heated (approximately 75° C.) at reflux for 51 h and then the solvents and volatile residues are distilled off at 110° C. (under vacuum of 1 mbar) for evaporation. The final product is subsequently washed (100 ml methanol) and dried; a yellow-coloured powder is thus obtained.

This powder is placed in methanol (100 ml per 15 g of powder) and the mixture is heated at reflux (65° C.) for 30 min. The solution is then left to cool to ambient temperature (approximately 20° C.) for crystallization of the monomer. The solid product obtained is isolated by filtration (Buchner filter). A white-coloured powder is thus obtained, after drying in an oven under vacuum at 50° C. overnight (reaction yield equal to approximately 82%).

The $^1$H NMR spectrum (500 MHz) of the Monomer M-3 thus synthesized, dissolved in d8-THF, confirmed its chemical structure, with the following results:

3.87 (s, 4H), 3.92 (s, 4H), 4.86 (s, 4H), 6.66-6.68 (d, 2H), 7.09-7.10 (d, 2H), 7.19-7.22 (d, 2H), 7.31 (s, 4H).

5.2. Synthesis of a Polybenzoxazine (Polymer P-4)

This synthesis is carried out according to the procedure diagrammatically represented in FIG. 11, as described in detail below, starting from two monomers: the benzoxazine of the invention obtained in the preceding stage (Monomer M-3) and the sulfur-comprising aromatic diol of formula (B-1) (4,4'-thiodiphenol; Monomer N-1) already described in FIG. 5; this being in the presence of sodium carbonate ($Na_2CO_3$; Sigma Aldrich product 13418), and of (anhydrous) solvents DMA (N,N-dimethylacetamide; Sigma Aldrich product 38839) and toluene (Acros Organics product No. 364411000). The two monomers (M-3 and N-1) are dried beforehand under vacuum (10 mbar) at 60° C. overnight, and likewise for the sodium carbonate but at a temperature of 150° C.

The synthesis is carried out in a 100-ml four-necked round-bottomed flask, equipped with a nitrogen inlet, a thermometer, a magnetic stirrer and a Dean-Stark separator surmounted by a condenser and by a distillation bridge (provided with a heating mantle). The apparatus is dried under vacuum using a hot air gun until the thermometer reaches a temperature of at least 100° C. in the reaction round-bottomed flask. Everything is left to cool to ambient temperature (20° C.) and then the apparatus is placed under a stream of nitrogen throughout the synthesis.

First of all, the Monomer M-3 (1 eq., 1.48 g, i.e. 2.79 mmol) of formula (A-3) and then the Monomer N-1 of formula (B-1) (1 eq., 0.61 g, i.e. 2.79 mmol) are then introduced into the round-bottomed flask. The addition is subsequently carried out of 20 ml of DMA (solvent of both monomers) and then, as base, of $Na_2CO_3$ (3 eq., 0.89 g, i.e. 8.36 mol) in suspension in 4 ml of toluene. Everything is purged under $N_2$ for 5 min and then the reaction medium is heated to 105° C. Once this temperature is reached (heating mantle temperature of approximately 115° C.), the distillation bridge of the Dean-Stark apparatus is heated to 110° C. (with the heating mantle) in order to facilitate the azeotropic distillation (water/toluene distillation) carried out for approximately 90 min. The temperature of the reaction medium is then gradually increased, in stationary phases of 10° C. every 30 min, until 130° C. is reached. The reaction medium is left at this temperature for 17 h and then it is left to cool to ambient temperature (20° C.). The reaction medium is subsequently distilled at 90° C. (vacuum 3 mbar), in order to remove solvents and volatile residues, and then the solid precipitate thus obtained is washed with 250 ml of distilled water; during this washing, in order to extract the carbonate, acid (1% aqueous HCl) is added dropwise until neutral pH is reached. The precipitate is once again washed with 100 ml of distilled water and dried under vacuum at 80° C. overnight (approximately 12 h).

Figure 11:
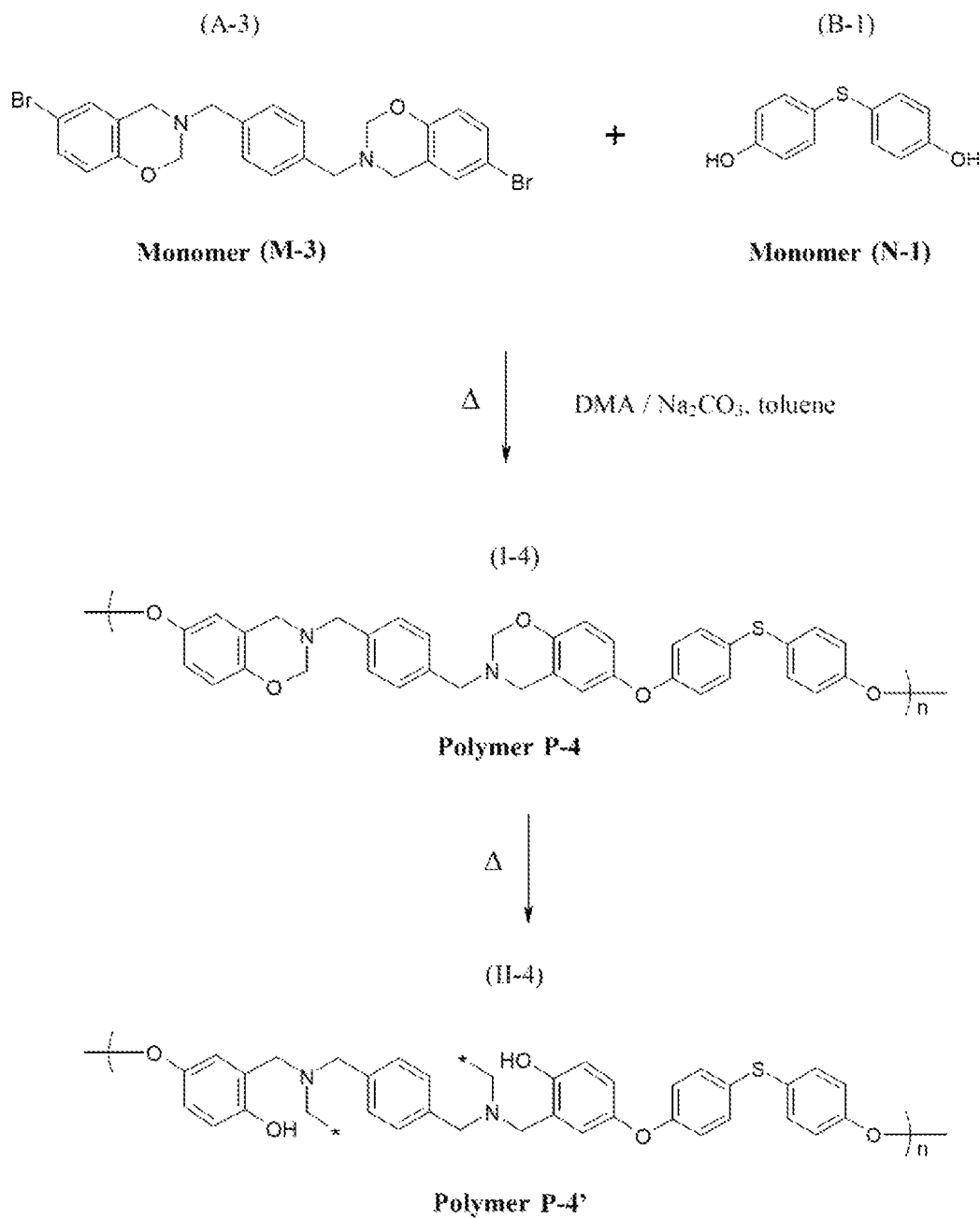

The Polymer P-4 of FIG. 11 was thus obtained, as attested to by the $^1$H NMR analysis (500 MHz) in the solvent d8-THF, which gave the following results:

7.35 (br, 4H), 7.21 (br, 2H), 7.08-7.14 (br, 6H), 6.62-6.68 (br, 6H), 4.87 (br, 4H), 3.1-4.4 (br, 8H). 3.1-4.4 (br, 8H).

This Polymer P-4, in the form of a red-coloured (rust-coloured) powder, was also analysed by DSC (Differential Scanning calorimetry) between −80° C. and +250° C. along a gradient of 10° C./min (Mettler Toledo "822-2" DSC device; nitrogen atmosphere). The analysis showed, in the first pass (between −80° C. and +250° C.), an exotherm (corresponding to the opening of the oxazine rings, and to the crosslinking of the polymer) above 200° C., with a maximum at approximately 230° C. During the second and third DSC passes carried out between −80° C. and +250° C., no apparent glass transition (Tg) was visible.

5.3. Test of Adhesion in a Metal/Rubber Composite

A portion (650 mg) of the Polymer P-4 prepared above was dissolved in 8 ml of DMA (N,N-dimethylacetamide; Sigma Aldrich product 38839), this being in order to form a solution, a fraction (0.7 ml) of which was subsequently deposited uniformly on a brass tape (film) having dimensions of 10 cm×2.5 cm and a thickness of 0.4 mm; the assembly was placed in an oven at 175° C. (air ventilation) for 5 min and then for an additional 5 min at 230° C. under vacuum in order, on the one hand, to remove any trace of solvent and, on the other hand, to at least partially (that is to say, completely or partially) open the oxazine rings of the polymer, this last stage being accompanied by a pronounced change in colour of the polymer, which changes to dark orange.

After cooling to ambient temperature, the tape provided at the surface with its thin (thickness 5 to 10 μm) layer of polybenzoxazine thus formed was subsequently subjected to a conventional two-stage adhesive coating operation (two baths adhesive coating), first of all by immersion in a first aqueous bath (approximately 94% water) based on epoxy resin (polyglycerol polyglycidyl ether, approximately 1%) and on isocyanate compound (caprolactam-blocked isocyanate compound, approximately 5%), which first adhesive coating stage is followed by a drying (2 min at 100° C.) and then a heat treatment (5 min at 200° C.). The tape thus treated was then immersed in a second aqueous bath of RFL adhesive (approximately 81% by weight of water) based on resorcinol (approximately 2%), on formaldehyde (approximately 1%) and on a rubber latex (approximately 16% of NR, SBR and VP/SBR rubbers); finally, it was dried in an oven at 130° C. for 2 min and then heat treated at 200° C. for 5 min.

The brass tape thus coated with the polybenzoxazine film and then coated with adhesive was subsequently placed between two layers of conventional rubber composition for a belt reinforcement of a passenger vehicle tyre, which composition is based on natural rubber, on carbon black and silica as filler and on a vulcanization system (sulfur and sulfenamide accelerator); this composition was devoid of cobalt salt. The metal/rubber composite test specimen thus prepared was then placed under a press and everything was cured (vulcanized) at 150° C. for 30 min under a pressure of 20 bar.

After vulcanization of the rubber, excellent adhesive bonding between the rubber matrix and the metal tape was obtained, despite the absence of cobalt salt in the rubber matrix; this is because, during peel tests (at 20° C.), it was found that the failure occurred systematically in the rubber matrix itself and not at the interphase between metal and rubber. Other adhesive bonding tests were carried out on a bright (uncoated) steel tape; they themselves also revealed an excellent adhesion to the rubber (systematic failure in the rubber matrix).

In conclusion, the benzoxazine according to the invention makes possible the synthesis of polymers giving the metal reinforcers the major advantage of being able subsequently to be adhesively bonded to rubber matrices using simple textile adhesives, such as RFL adhesives, or else directly (that is to say, without employing such adhesives) to these rubber matrices, for example when the latter contain appropriate functionalized unsaturated elastomers, such as epoxidized elastomers. Thus, use may be made of metal reinforcers coated or not coated with adhesive metal layers, such as brass, and also of surrounding rubber matrices devoid of metal salts, in particular of cobalt salts.

Moreover, this constituting a significant advantage in comparison with the other known polymers described in the introduction to the present document, the polybenzoxazines resulting from the benzoxazines of the invention have the remarkable ability, at high temperature, to open their oxazine rings and to thus result in a thermosetting polyphenol resin structure. This confers a better thermal stability on them. Finally, their specific microstructure makes it possible, very advantageously, to adjust the flexibility of the molecule according to the particular applications targeted.

The invention claimed is:

1. A halogenated benzoxazine compound corresponding to the formula:

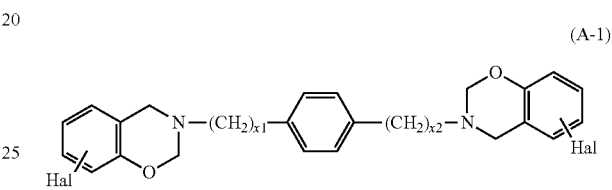

(A)

in which:
Hal represents at least one halogen;
each benzene nucleus of the two oxazine rings bears at least one halogen; and
$Z_1$ and $Z_2$, which are identical or different, represent an aliphatic, at least divalent, bonding group comprising at least one carbon atom and optionally at least one heteroatom chosen from O, S, N and P.

2. The halogenated benzoxazine compound according to claim 1, wherein $Z_1$ and $Z_2$, which are identical or different, represent an aliphatic group comprising from 1 to 12 carbon atoms.

3. The halogenated benzoxazine compound according to claim 2, wherein $Z_1$ and $Z_2$, which are identical or different, represent a (poly)alkylene sequence comprising from 1 to 8 carbon atoms.

4. The halogenated benzoxazine compound according to claim 3 corresponding to the formula:

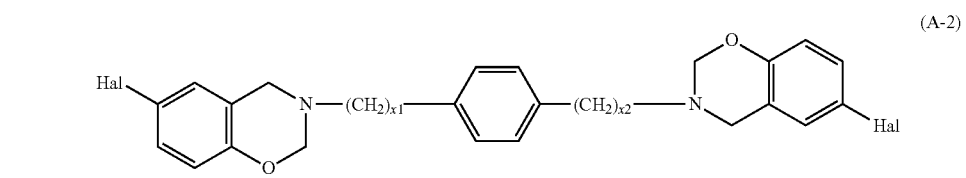

(A-1)

in which $x_1$ and $x_2$, which are identical or different, represent an integer from 1 to 8.

5. The halogenated benzoxazine compound according to claim 1, wherein Hal represents bromine, chlorine or fluorine.

6. The halogenated benzoxazine compound according to claim 1, wherein each benzene nucleus of the two oxazine rings bears a single halogen.

7. The halogenated benzoxazine compound according to claim 6, wherein the halogen borne by each benzene nucleus of the two oxazine rings is located in the para position with respect to the oxygen of the oxazine ring.

8. The halogenated benzoxazine compound according to claim 1, wherein Hal represents bromine.

9. The halogenated benzoxazine compound according to claim 4 corresponding to the formula:

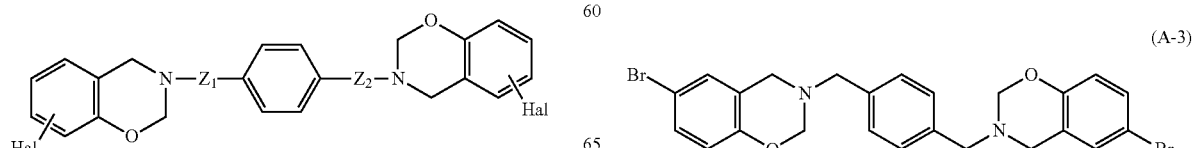

(A-2)

in which $x_1$ and $x_2$, which are identical or different, represent an integer from 1 to 8.

10. The halogenated benzoxazine compound according to claim 9 corresponding to the formula:

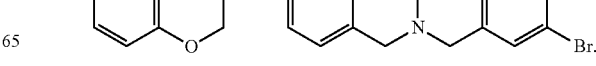

(A-3)

11. A polybenzoxazine made by polycondensation of at least one compound corresponding to the formula:

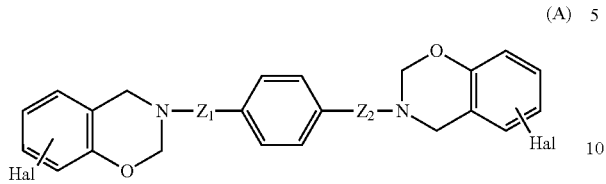

(A)

in which:
Hal represents at least one halogen;
each benzene nucleus of the two oxazine rings bears at least one halogen; and
$Z_1$ and $Z_2$, which are identical or different, represent an aliphatic, at least divalent, bonding group comprising at least one carbon atom and optionally at least one heteroatom chosen from O, S, N and P.

12. The polybenzoxazine according to claim 11 made by polycondensation of a compound corresponding to formula (A), as a first monomer, with at least an aromatic diol or thiol compound, as a second monomer.

13. The polybenzoxazine according to claim 12, wherein the aromatic diol or thiol compound corresponds to the formula (B):

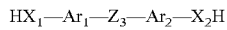

in which:
$X_1$ and $X_2$, which are identical or different, represent O or S;
$Ar_1$ and $Ar_2$, which are identical or different, represent a phenylene group; and
$Z_3$ represents O or $(S)_n$, n representing an integer equal to or greater than 1.

14. The polybenzoxazine according to claim 13, wherein the aromatic diol or thiol compound corresponds to at least one of the formulae (B-1), (B-2) or (B-3):

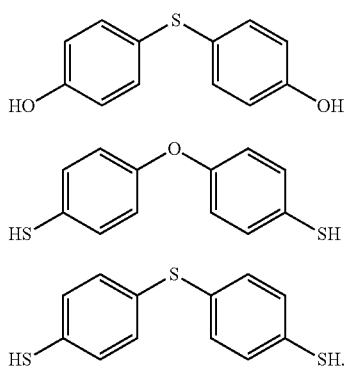

15. The polybenzoxazine according to claim 11, wherein each benzene nucleus of the two oxazine rings bears a single halogen.

16. A process for the synthesis of a polybenzoxazine comprising the step of:

polycondensating a compound corresponding to the formula:

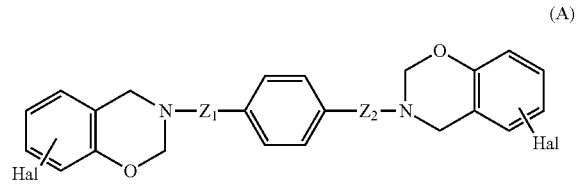

(A)

in which:
Hal represents at least one halogen;
each benzene nucleus of the two oxazine rings bears at least one halogen; and
$Z_1$ and $Z_2$, which are identical or different, represent an aliphatic, at least divalent, bonding group comprising at least one carbon atom and optionally at least one heteroatom chosen from O, S, N and P.

17. The process according to claim 16, wherein the compound corresponding to formula (A), as a first monomer, is polycondensated with at least an aromatic diol or thiol compound, as a second monomer.

18. The process according to claim 17, wherein the aromatic diol or thiol compound corresponds to the formula (B):

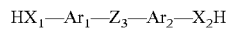

in which:
$X_1$ and $X_2$, which are identical or different, represent O or S;
$Ar_1$ and $Ar_2$, which are identical or different, represent a phenylene group; and
$Z_3$ represents O or $(S)_n$, n representing an integer equal to or greater than 1.

19. The process according to claim 18, wherein the aromatic diol or thiol compound corresponds to at least one of formulae (B-1), (B-2) or (B-3) below:

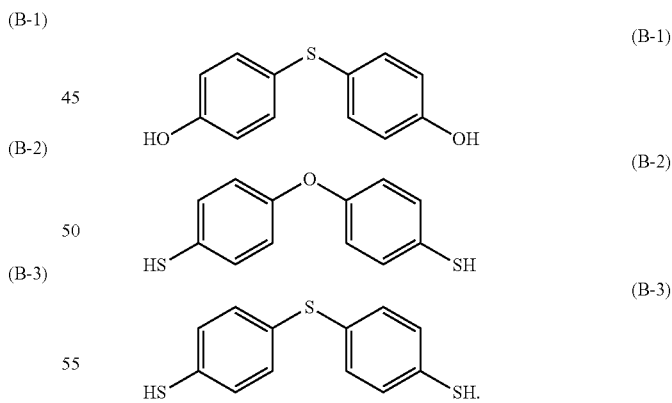

20. The process according to claim 16, wherein each benzene nucleus of the two oxazine rings bears a single halogen.

* * * * *